US010966612B2

(12) United States Patent
Newswanger

(10) Patent No.: US 10,966,612 B2
(45) Date of Patent: Apr. 6, 2021

(54) EXPANDING BEAM OPTICAL ELEMENT

(71) Applicant: Open Water Internet Inc., San Francisco, CA (US)

(72) Inventor: Craig Newswanger, Oakland, CA (US)

(73) Assignee: Open Water Internet Inc., San Francisco, CA (US)

(*) Notice: Subject to any disclaimer, the term of this patent is extended or adjusted under 35 U.S.C. 154(b) by 85 days.

(21) Appl. No.: 16/439,631

(22) Filed: Jun. 12, 2019

(65) Prior Publication Data

US 2019/0380587 A1 Dec. 19, 2019

Related U.S. Application Data

(60) Provisional application No. 62/684,900, filed on Jun. 14, 2018.

(51) Int. Cl.
*G01B 9/02* (2006.01)
*A61B 5/00* (2006.01)
*G02B 7/00* (2021.01)

(52) U.S. Cl.
CPC ............ *A61B 5/0059* (2013.01); *G02B 7/002* (2013.01)

(58) Field of Classification Search
CPC .... A61B 5/0059; G02B 7/002; G02B 27/095; G02B 26/128; G02B 26/106; G02B 27/0955; G02B 5/32; G02B 7/04; G03H 1/0406
See application file for complete search history.

(56) References Cited

U.S. PATENT DOCUMENTS

| 6,172,760 | B1 | 1/2001 | Son |
| 6,956,650 | B2 | 10/2005 | Boas |
| 7,119,906 | B2 | 10/2006 | Pepper |
| 7,460,248 | B2 | 12/2008 | Kurtz |
| 7,551,809 | B2 | 6/2009 | Taira |
| 7,610,082 | B2 | 10/2009 | Chance |
| 7,647,091 | B2 | 1/2010 | Ntziachristos |
| 7,728,986 | B2 | 6/2010 | Lasker |
| 7,804,070 | B1 | 9/2010 | Pan |
| 7,821,640 | B2 | 10/2010 | Koenig |
| 7,822,468 | B2 | 10/2010 | Stammes |
| 7,826,878 | B2 | 11/2010 | Alfano |
| 7,898,649 | B2 | 3/2011 | Masumura |
| 7,965,389 | B2 | 6/2011 | Da Silva |

(Continued)

OTHER PUBLICATIONS

Arridge et al. Nonuniqueness in diffusion-based optical tomography, Optics Letters, Jun. 1, 1998, vol. 23, No. 11, pp. 882-884.

(Continued)

*Primary Examiner* — David P Porta
*Assistant Examiner* — Mamadou Faye
(74) *Attorney, Agent, or Firm* — Freestone Intellectual Property Law PLLC; Aaron J. Visbeek

(57) ABSTRACT

A refractive component includes at least one reflection surface and at least one diffractive optical element. The refractive component is configured to receive a light beam and the light beam expands within the refractive component and is reflected by the at least one reflection surface. The diffractive optical element is configured to receive the light beam reflected from the at least one reflection surface, collimate the light beam, and redirect the light beam out of the refractive component.

21 Claims, 14 Drawing Sheets

(56) References Cited

U.S. PATENT DOCUMENTS

| | | |
|---|---|---|
| 7,983,740 B2 | 7/2011 | Culver |
| 7,928,896 B2 | 8/2011 | Jin |
| 8,014,847 B2 | 9/2011 | Shastri |
| 8,120,784 B2 | 2/2012 | Da Silva |
| 8,170,651 B2 | 5/2012 | Lorenzo |
| 8,239,006 B2 | 8/2012 | Zhu |
| 8,263,947 B2 | 9/2012 | Da Silva |
| 8,289,502 B2 | 10/2012 | Yoshida |
| 8,326,567 B2 | 12/2012 | Masumura |
| 8,330,642 B2 | 12/2012 | Jin |
| 8,355,131 B2 | 1/2013 | Bakker |
| 8,357,915 B2 | 1/2013 | Guyon |
| 8,374,409 B2 | 2/2013 | Jochemsen |
| 8,416,421 B2 | 4/2013 | Wang |
| 8,450,674 B2 | 5/2013 | Yang |
| 8,451,450 B2 | 5/2013 | Heng |
| 8,520,921 B2 | 8/2013 | Ziegler |
| 8,525,998 B2 | 9/2013 | Yaqoob |
| 8,527,242 B2 | 9/2013 | Granot |
| 8,531,662 B2 | 9/2013 | Van Der Mark |
| 8,563,932 B2 | 10/2013 | Fang |
| 8,634,077 B2 | 1/2014 | Hu |
| 8,649,015 B2 | 2/2014 | Ichihara |
| 8,917,442 B2 | 3/2014 | Baym |
| 8,717,574 B2 | 5/2014 | Yang |
| 8,814,795 B2 | 8/2014 | Derode |
| 8,817,255 B2 | 8/2014 | Masumura |
| 8,830,573 B2 | 9/2014 | Cui |
| 8,847,175 B2 | 9/2014 | Laidevant |
| 8,937,284 B2 | 1/2015 | Fang |
| 8,954,130 B2 | 2/2015 | Masumura |
| 8,976,433 B2 | 3/2015 | Masumura |
| 9,012,869 B2 | 4/2015 | Andersson-Engels |
| 9,036,970 B2 | 5/2015 | Guyon |
| 9,037,216 B2 | 5/2015 | Hielscher |
| 9,057,695 B2 | 6/2015 | Masumura |
| 9,131,851 B2 | 9/2015 | Fukutani |
| 9,134,229 B2 | 9/2015 | Lesage |
| 9,179,842 B2 | 11/2015 | Nakaji |
| 9,207,171 B2 | 12/2015 | Nadakuditi |
| 9,234,841 B2 | 1/2016 | Wang |
| 9,282,932 B2 | 3/2016 | Kudo |
| 9,297,752 B2 | 3/2016 | Shimokawa |
| 9,304,490 B2 | 4/2016 | Masumura |
| 9,313,423 B2 | 4/2016 | Wang |
| 9,335,604 B2 | 5/2016 | Popovich |
| 9,335,605 B2 | 5/2016 | Wang |
| 9,341,569 B2 | 5/2016 | 'T Hooft |
| 9,354,166 B2 | 5/2016 | Judkewitz |
| 9,373,020 B2 | 6/2016 | Kudo |
| 9,407,796 B2 | 8/2016 | Dinten |
| 9,427,213 B2 | 8/2016 | Suzuki |
| 9,480,425 B2 | 11/2016 | Culver |
| 9,486,142 B2 | 11/2016 | Hielscher |
| 9,488,574 B2 | 11/2016 | Koehler |
| 9,509,956 B2 | 11/2016 | Piestun |
| 9,622,663 B2 | 4/2017 | Fang |
| 9,689,797 B2 | 6/2017 | Sun |
| 9,724,489 B2 | 8/2017 | Barbour |
| 9,730,649 B1 | 8/2017 | Jepsen |
| 9,750,413 B2 | 9/2017 | Sandusky |
| 2007/0013999 A1* | 1/2007 | Marks ............... G01Q 60/22 359/368 |
| 2007/0232861 A1* | 10/2007 | Kohno ............... A61B 5/0084 600/160 |
| 2010/0016732 A1 | 1/2010 | Wells |
| 2010/0268042 A1* | 10/2010 | Wang ............... G01N 29/2418 600/322 |
| 2012/0070817 A1 | 3/2012 | Wang et al. |
| 2014/0081096 A1 | 3/2014 | Baym |
| 2014/0114181 A1 | 4/2014 | Wu |
| 2014/0303473 A1 | 10/2014 | Nanaumi |
| 2015/0182120 A1* | 7/2015 | Sumi ............... A61C 19/04 433/29 |
| 2015/0182121 A1 | 7/2015 | Barbour |
| 2015/0238092 A1 | 8/2015 | Masumura |
| 2015/0241342 A1 | 8/2015 | Zhou |
| 2015/0346027 A1 | 12/2015 | Khare |
| 2015/0351635 A1 | 12/2015 | Cerussi |
| 2016/0085135 A1 | 3/2016 | Park |
| 2016/0157723 A1 | 6/2016 | Kanick |
| 2016/0262723 A1 | 9/2016 | Zhu |
| 2016/0363527 A1 | 12/2016 | Ruan |
| 2017/0118423 A1 | 4/2017 | Zhou |
| 2017/0163946 A1 | 6/2017 | Komanduri |
| 2017/0168565 A1 | 6/2017 | Cohen |
| 2017/0202633 A1 | 7/2017 | Liu |
| 2017/0230555 A1 | 8/2017 | Tabirian |
| 2017/0231501 A1 | 8/2017 | Culver |
| 2019/0137255 A1* | 5/2019 | Chong ............... G01B 9/02049 |

OTHER PUBLICATIONS

Hofmann et al. Differential light detector, Rev. Sci. Instrum, Feb. 1979, vol. 50, No. 2, pp. 249-252.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Peng et al. Low loss liquid crystals for infrared applications, Liquid Crystal, 2014, vol. 41, No. 11, pp. 1545-1552.

* cited by examiner

EXPANDING BEAM OPTICAL ELEMENT

CROSS-REFERENCE TO RELATED APPLICATIONS

This application claims priority to U.S. provisional Application No. 62/684,900 filed Jun. 14, 2018, which is hereby incorporated by reference.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, improve accuracy, reduce size and/or reduce cost.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1A:
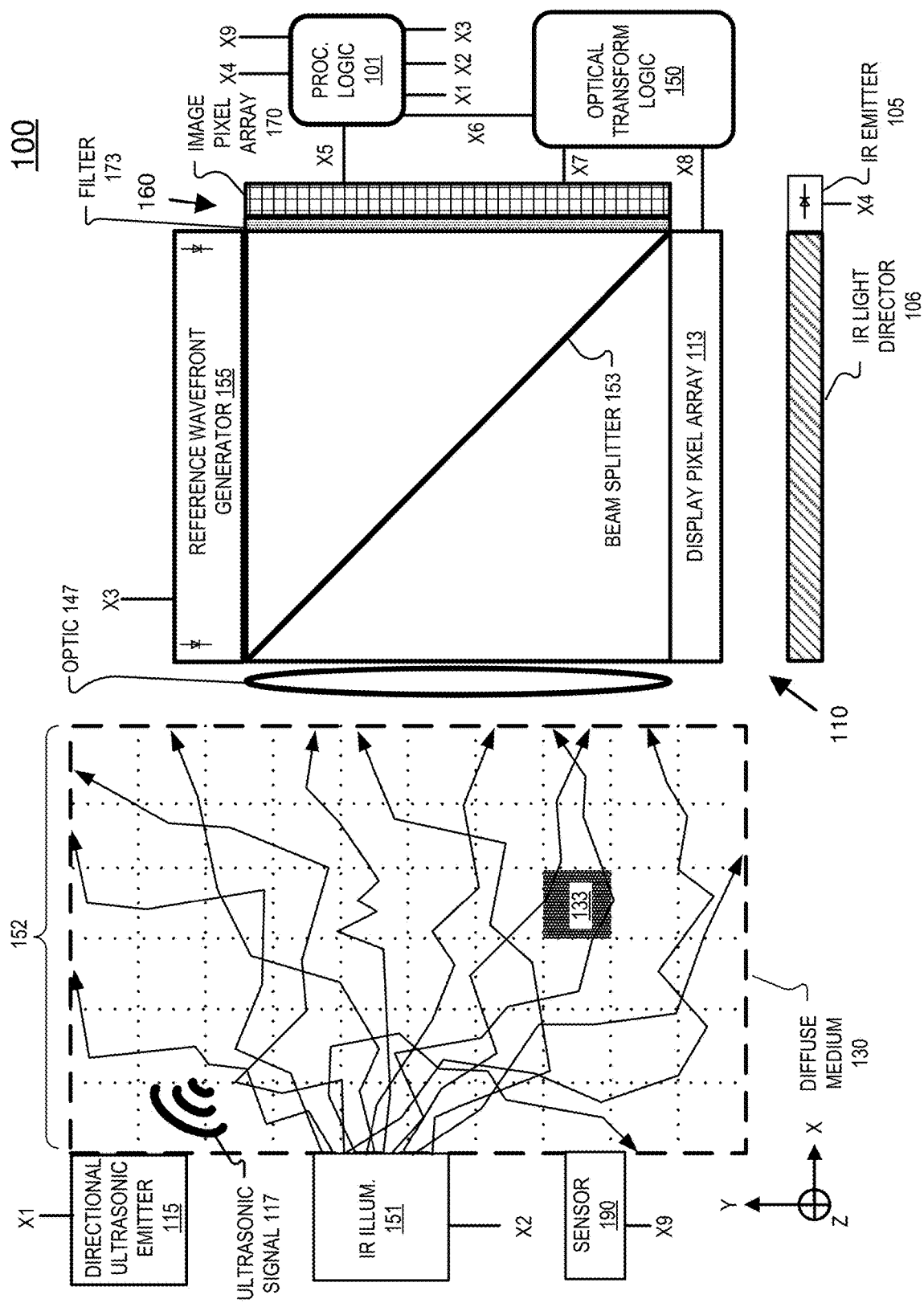
FIGS. 1A-1C illustrate an example imaging system that includes a display pixel array, an image pixel array, and a beam splitter, in accordance with an embodiment of the disclosure.

Embodiments of a system, device, and optical element for expanding a beam described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

This disclosure will generally describe imaging a diffuse medium in the context of human tissue in the medical context, however, the content of this disclosure may be applied to medical imaging, navigation, security, scientific research, or other contexts that image diffuse mediums or objects.

Human tissue is translucent to infrared light and to at least some wavelengths of visible light, although different parts of the human body (e.g. skin, blood, bone) exhibit different absorption coefficients. Researchers have attempted to use the properties of infrared light for medical imaging purposes, but size and cost constraints have been prohibitive for wide-scale adoption. Illuminating tissue and other diffuse mediums with visible light and near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least scattered (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultra-fast shutters on sensors that are able to image at the speed of light and the systems are overall very expensive and bulky. TOF imaging also requires an input of approximately 10-100 fold (or more) light intensity into the body than is received at the detector. Thus, efficacy and power limitations as well as safety limits on input intensity limit TOF imaging resolution, depth and utility.

In contrast to TOF imaging, some embodiments of the disclosure may illuminate a diffuse medium with an infrared light or visible light while an ultrasound emitter is focused on a particular voxel. A photosensitive element (e.g. an image sensor) may capture an interference pattern generated by the infrared exit signal (object beam) interfering with an infrared reference wavefront to generate an optical measurement of the particular voxel. To accomplish this, a proper reference beam to interfere with the infrared exit signal across the image sensor must be generated. It may be of particular benefit to generate the proper infrared reference wavefront in a compact form factor. The infrared reference wavefront may be collimated and delivered at a particular angle with respect to a pixel plane of the image sensor. Furthermore, the delivery of the reference beam should still allow the infrared exit signal (or the interference signal of the infrared reference signal and the infrared reference wavefront) to reach the photosensitive element (e.g. image sensor). Embodiments of the disclosure provide an optical element to direct infrared laser light from an optical fiber to a photosensitive element that may be collimated, at a precise angle, and/or appropriately sized to cover the photosensitive element. The optical element may utilize one or more reflection surfaces and at least one diffractive optical element (e.g. a hologram) to fold the optical path of an expanding beam into a reference wavefront with particular characteristics. These embodiments and others will be described in more detail with references to FIGS. 1A-7.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise. For the purposes of the disclosure, visible light has a wavelength from approximately 400 nm to 700 nm and near-infrared light has a wavelength from approximately 700 nm to 1400 nm.

Figure 1B:
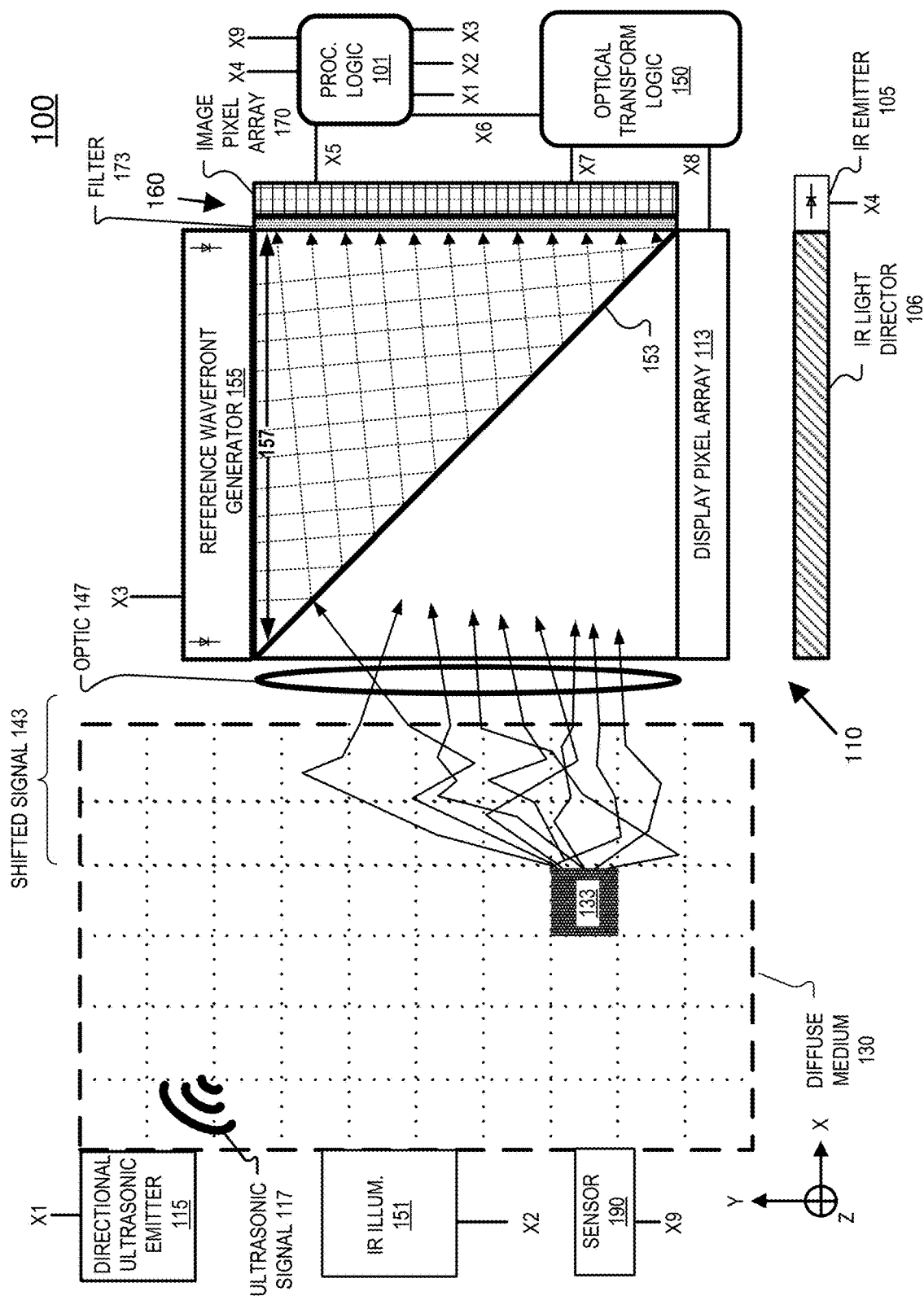
Figure 1C:
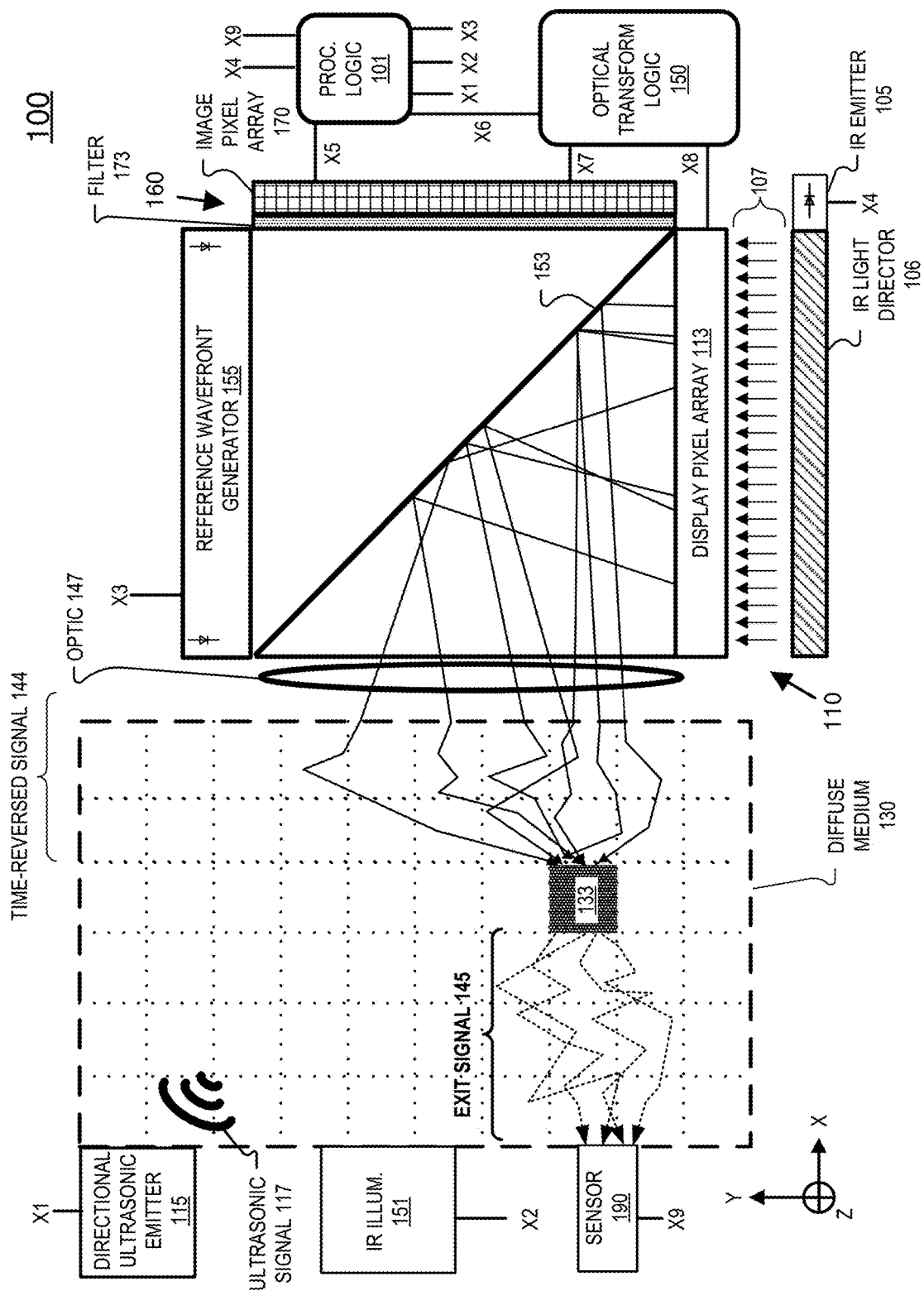

FIGS. 1A-1C illustrate an example imaging system that includes a display pixel array, an image pixel array, and a beam splitter, in accordance with an embodiment of the disclosure. In FIG. 1A, imaging system 100 includes processing logic 101, a spatial light modulator (SLM) 110, and image module 160. Imaging module 160 includes image pixel array 170 and filter(s) 173. In FIG. 1A, imaging system 100 also includes a directional ultrasonic emitter 115 coupled to be driven by processing logic 101. In FIG. 1A, SLM 110 includes an infrared emitter 105, an infrared light director 106, and a display pixel array 113. Display pixel array 113 may be an LCD (liquid crystal display), for example. The LCD display may be an active-matrix (using thin-film-transistors) or a passive matrix LCD. In one embodiment, the LCD display has pixels that are smaller than 7 microns. In other embodiments, SLM 110 may include a reflective architecture such as a liquid-crystal-on silicon (LCOS) display being illuminated by infrared light, for example. Other known transmissive and reflective display technologies may also be utilized as SLM 110. System 100 may include a plurality of discrete devices that incorporate components of system 100, in some embodiments.

Processing logic 101 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 101 to store instructions to execute operations and/or store data. A "memory" or "memories" described in this disclosure may include volatile or non-volatile memory architectures.

System 100 includes an infrared illuminator 151. Processing logic 101 is coupled to selectively activate IR illuminator 151 via output X2, in the illustrated embodiment. Infrared illuminator 151 may include an infrared laser generating a general illumination emission 152. Of course, an infrared laser may generate monochromatic coherent infrared light. Monochromatic light may be defined as light within a 4 nm frequency band, for example. The infrared light that IR illuminator 151 emits may be centered around a frequency in the 680-1000 nm range. In one embodiment, the infrared light that IR illuminator 151 emits may be centered around a frequency in the 1600-1700 nm range. In one example, IR illuminator 151 generates monochromatic light centered around 680 nm. In one example, IR illuminator 151 generates monochromatic light centered around 850 nm. The infrared illuminator 151 is disposed to direct the general illumination emission 152 into the diffuse medium 130. In the context of tissue, general illumination emission 152 will be significantly scattered within tissue within as little as 1 cm of depth into the tissue when tissue is the diffuse medium 130. At least a portion of the general illumination emission 152 will encounter voxel 133, as illustrated in FIG. 1A.

System 100 also includes an ultrasonic emitter 115. Ultrasonic emitter 115 is configured to focus an ultrasonic signal 117 to a point in three-dimensional space. In the medical context, the ultrasonic emitter 115 is configured to focus an ultrasonic signal 117 to a voxel within the human body. The voxel may be within the brain, abdomen, or uterus, for example. Processing logic 101 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example. Focusing an ultrasonic signal 117 to a given voxel of tissue (e.g. voxel 133) influences the portion of illumination emission 152 that encounters the voxel by wavelength-shifting that portion of illumination emission 152 that propagates through that voxel.

In FIG. 1B, the wavelength-shifted portion of the general illumination emission 152 is illustrated as shifted infrared imaging signal 143. Being influenced by ultrasonic signal 117, shifted signal 143 has a different wavelength (hereinafter referred to as lambda-two) than general illumination emission 152 (referred to as lambda-one). In some embodiments, the delta between lambda-one and lambda-two may be less than 1 nanometer. In an embodiment, the delta between lambda-one and lambda-two may be less than 20 femtometer.

System 100 receives (at least a portion of) shifted infrared imaging signal 143. An input optic 147 may optionally be included in system 100. Input optic 147 may receive shifted signal 143 and direct the shifted signal 143 to be incident on image pixel array 170. In one embodiment, input optic 147 is configured to filter out an angled portion of the shifted signal 143. In one embodiment, the angled portion of the shifted signal 143 has a plus-or-minus angle of incidence upon the input optic 147 that is higher than an angle threshold. In one embodiment, the sine of twice the angle threshold is approximately equivalent to a wavelength of the shifted signal 143 (lambda-two) divided by twice a distance between two pixels of the image pixel array 170. In one embodiment, the angle threshold is between five and seven degrees.

Still referring to FIG. 1B, reference wavefront generator 155 generates an infrared reference wavefront 157 having the lambda-two wavelength so that infrared reference wavefront 157 interferes with the incoming shifted signal 143. Reference wavefront generator 155 may include one or more laser diodes and corresponding optics to generate a substantially uniform wavefront. Processing logic 101 is coupled to selectively activate reference wavefront generator 155 via output X3, in the illustrated embodiment.

A first portion of the infrared reference wavefront 157 is redirected to the image pixel array 170 by beam splitter 153 while a second remaining portion of wavefront 157 passes through beam splitter 153. Shifted signal 143 encounters beam splitter 153 and a first portion of the shifted signal 143 passes through beam splitter 153 while the remaining second portion of the shifted signal 143 is reflected by beam splitter 153. The first portion of the shifted signal 143 that passes through beam splitter 153 interferes with the first portion of wavefront 157 that is redirected to image pixel array 170 and image pixel array 170 captures an infrared image of the interference between shifted signal 143 and infrared reference wavefront 157.

In one embodiment, reference wavefront generator 155 is disposed to deliver the infrared reference wavefront 157 to the image pixel array 170 at an angle to a pixel plane of the image pixel array 170. Image pixel array 170 may include image pixels disposed in a two-dimensional rows and columns that define the pixel plane of the image pixel array 170. In one embodiment, the angle is between five and seven degrees so that the infrared reference wavefront 157 encounters the image pixels of image pixel array 170 at a non-orthogonal angle. Angling the infrared reference wavefront 157 may change the interference orientation and size between shifted signal 143 and wavefront 157, which may enable better signal isolation at the image pixel array 170. Processing logic 101 is coupled to initiate the image capture by image pixel array 170 via output X5, in the illustrated embodiment.

A linear polarizer may be included in system 100 to polarize shifted signal 143 to have the same polarization orientation as infrared reference wavefront 157. The light source of reference wavefront generator 155 may generate linear polarized light which imparts a polarization orientation to infrared reference wavefront 157. The linear polarizer may be included in optic 147, filter 173, or in a linear polarizer disposed between optic 147 and filter 173.

In the illustrated embodiment, an infrared filter 173 is disposed between beam splitter 153 and image pixel array 170. Infrared filter 173 may pass the wavelength of infrared light emitted by reference wavefront generator 155 (lamda-two) and reject ambient light in a bandpass that is 10 nm or greater.

Image pixel array 170 may be implemented with an a-Si (amorphous Silicon) thin film transistors, in some embodiments or a CMOS (Complementary Metal-Oxide-Semiconductor) image sensor, in some embodiments. Image pixel array 170 can be a commercially available image sensor. In one embodiment, image pixel array 170 has image pixels having a pixel pitch of 3.45 microns. In one embodiment, image pixel array 170 has image pixels having a pixel pitch of 1.67 microns. The pixel resolution of image pixel array 170 may vary depending on the application. In one embodiment, the image pixel array 170 is 1920 pixels by 1080 pixels. In one embodiment, the image pixel array is 40 Megapixels or more. Image pixel array 170 can capture an infrared image of an interference between shifted signal 143 and IR reference wavefront 157 by measuring the image charge generated in each pixel during a given integration period that is determined by an electronic shutter. The electronic shutter may be a global shutter (where each pixel measures the incident light during a same time period) or a rolling shutter. The electronic shutter can be actuated by processing logic 101 via input/output X5. Input/output X5 may include digital input/output lines as well as a data bus. Image pixel array 170 is communicatively coupled to optical transform logic 150 to send the captured infrared image(s) to optical transform logic 150 for further processing. In some embodiments, the integration period of the pixels of the image pixel array 170 is determined by the length of a laser pulse. Image pixel array 170 may include a local (on-board) digital signal processor (DSP), in some embodiments, and optical transform logic 150 may receive the captured infrared images from the DSP.

Optical transform logic 150 is coupled to image pixel array 170 via communication channel X7, in the illustrated embodiment. Optical transform logic is also communicatively coupled to processing logic 101 via communication channel X6. Optical transform logic 150 is coupled to receive the captured infrared image from the image pixel array and provide a holographic pattern to be driven onto the display pixel array 113. The optical transform logic 150 is configured to extract phase data of the interference captured by the infrared image and the holographic pattern is generated from the phase data. A more detailed description of example optical transform logic is described in U.S. patent application Ser. No. 15/942,480, which is hereby incorporated by reference.

Referring now to FIG. 1C, display pixel array 113 is configured to generate an infrared holographic imaging signal 144 (reconstruction of signal 143) according to a holographic pattern driven onto the array 113. Optical transform logic 150 is coupled to provide the array 113 the holographic pattern via communication channel X8.

In FIG. 1C, display pixel array 113 is illustrated as a transmissive LCD that is illuminated by infrared wavefront 107. In the illustrated embodiment, infrared (IR) emitter 105 is coupled to be driven by output X4 of processing logic 101. When processing logic 101 turns on (activates) IR emitter 105, infrared light propagates into IR light director 106. IR light director 106 may be a light guide plate similar to those found in conventional edge lit LCDs. IR light director 106 may be a slim prism utilizing TIR (total internal reflection). IR light director 106 redirects the infrared light toward display pixel array 113. IR light director 106 may include a sawtooth grating to redirect the infrared light toward array 113. IR emitter 105 is an infrared laser diode that emits monochromatic infrared light, in one embodiment.

Steerable infrared beams can be generated by SLM 110 by driving different holographic patterns onto display pixel array 113. Each different holographic pattern can steer (focus) the infrared light in a different direction. The directional nature of the infrared beam is influenced by the constructive and destructive interference of the infrared light emitted from the pixels of SLM 110. As an example, a holographic pattern that includes different "slits" at different locations can generate different infrared beams. The "slits" can be generated by driving all the pixels in the display pixel array 113 to "black" (not transmissive) except for the pixels where the "slits" are located are driven to be "white" (transmissive) to let the infrared light propagate through. The pixel size of display pixel array 113 may be 1 micron, although in some embodiments pixels sized up to 10 times the wavelength of the infrared light can be used. In one example, if IR emitter 105 is an 850 nm laser diode, the pixel size of SLM 110 may be 850 nm. The pixel size influences the angular spread of a hologram since the angular spread is given by the Grating Equation:

$$\sin(\theta) = m\lambda/d \qquad \text{(Equation 1)}$$

where θ is the angular spread of light, m is an integer number and the order of diffraction, and d is the distance of two pixels (a period). Hence, smaller pixel size generally yields more design freedom for generating holographic beams, although pixels sizes that are greater than the wavelength of light can also be used to generate holographic imaging signals. Display pixel array 113 may include square pixels (rather than the rectangular pixels in conventional RGB LCDs) so that the Grating Equation is applicable in both the row dimension and column dimension of the display pixel array 113.

In the illustrated embodiment, processing logic 101 selectively activates infrared emitter 105 and infrared light director 106 directs the infrared light to illuminate display pixel array 113 as infrared wavefront 107 while the holographic pattern is driven onto array 113. Infrared wavefront 107 is the same wavelength as infrared reference wavefront 157. Processing logic 101 may deactivate reference wavefront generator 155 while display pixel array 113 is being illuminated by infrared wavefront 107. Processing logic 101 may be configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Display pixel array 113 generates an infrared holographic imaging signal when the holographic pattern is illuminated by infrared wavefront 107 and the infrared holographic imaging signal is redirected by beam splitter 153 to exit system 100 as a reconstruction 144 (in reverse) of the shifted signal 143 that entered system 100. Reconstructed signal 144 follows (in reverse) whatever scattered path that shifted signal 143 took from voxel 133 to beam splitter 153 so reconstructed signal 144 is essentially "focused" back onto voxel 133.

Voxel 133 may absorb or scatter reconstructed signal 144 according to biological and/or optical characteristics of voxel 133 and sensors may measure an exit signal 145 of the reconstructed signal 144 that encounters voxel 133. System 100 may optionally include a sensor 190 coupled to processing logic 101 via an input/output X9 to initiate light measurement of exit signal 145 and pass the light measurement to processing logic 101. Although exit signal 145 is illustrated as being directed to sensor 190, the illustrated exit signal 145 is only a portion of the exit signal 145 that will be generated from signal 144 encountering voxel 133 and exit signal 145 will have many exit points from diffuse medium in addition to the illustrated portion of exit signal 145. The sensors that measure this exit signal may simply measure the amplitude of the exit signal. Sensor 190 may be a photodiode or a CMOS image sensor, for example. In one embodiment, the image pixel array 170 is used to measure the amplitude and/or phase of exit signal 145. The amplitude and/or phase of the exit signal 145 may be used to generate an image of diffuse medium 130. A reconstructed signal 144 may be directed to voxel 133 multiple times (with multiple corresponding measurements of exit signal 145) so that biological changes in voxel 133 may be recorded over a time range.

System 100 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array gives display pixel array 113 the ability to generate steerable holographic infrared beams that can focus an infrared signal (e.g. 144) to different voxels in three-dimensional space to facilitate the raster scanning of diffuse medium 130.

In one embodiment, processing logic 101 is configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Figure 2A:
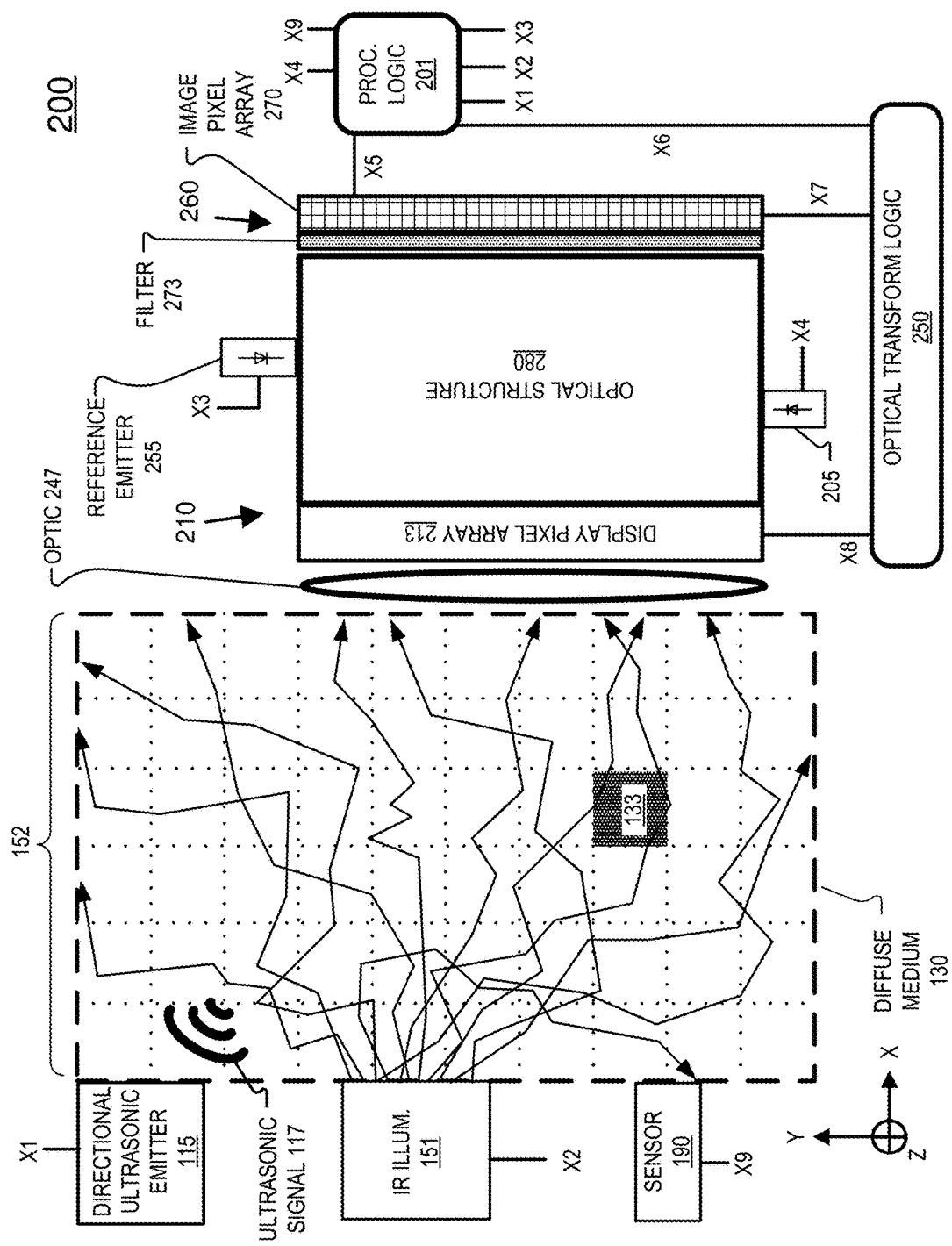
FIGS. 2A-2C illustrate an example imaging system that includes an image pixel array receiving an exit signal through a display pixel array, in accordance with an embodiment of the disclosure.
Figure 2B:
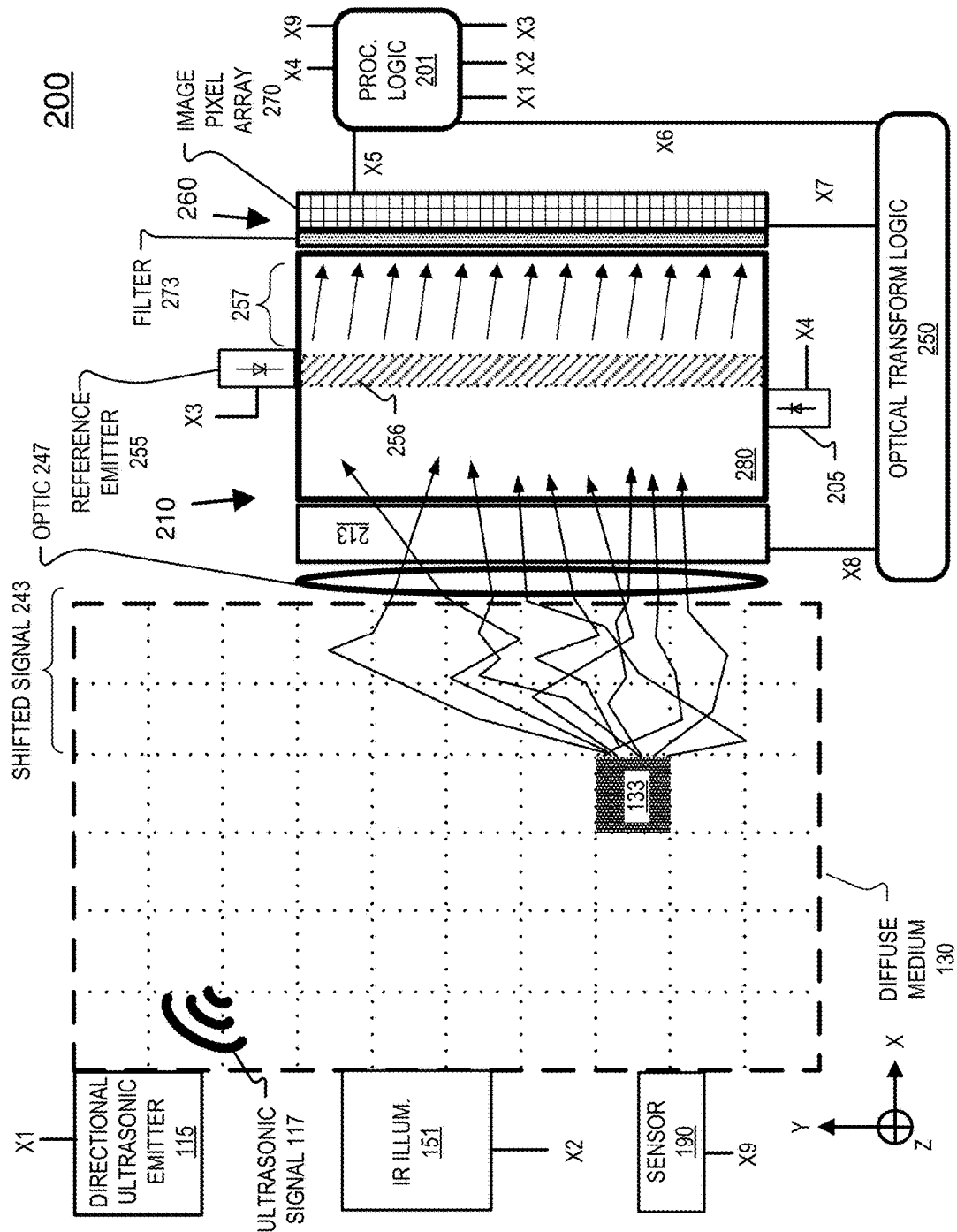
Figure 2C:
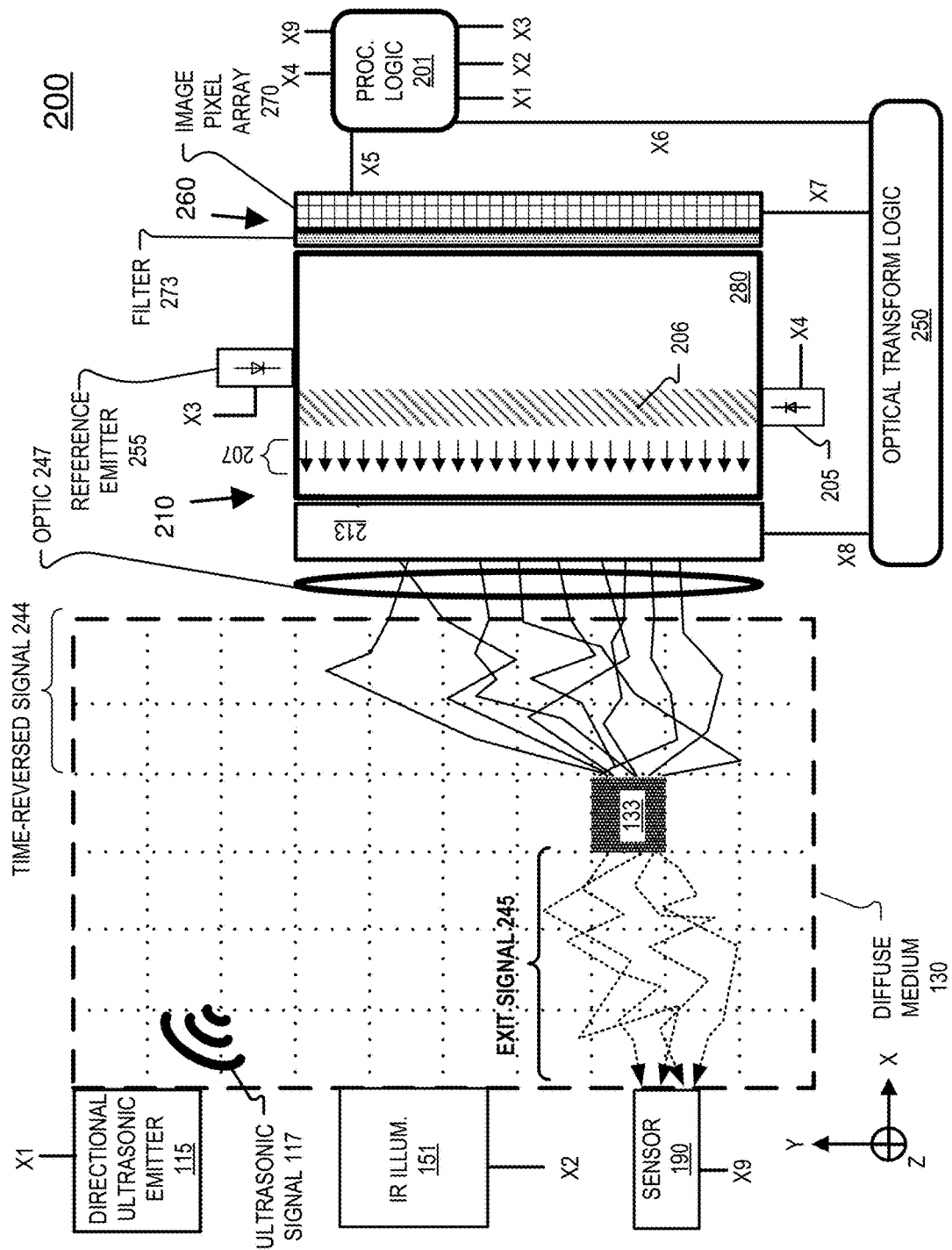

FIGS. 2A-2C illustrate an example imaging system 200 that includes an optical structure disposed between a display pixel array and an image pixel array, in accordance with an embodiment of the disclosure. System 200 illustrated in FIGS. 2A-2C functions similarly to system 100 of FIGS. 1A-1C although there are differences associated with the different positioning of the SLM 210, the imaging module 260, and the addition of optical structure 280.

Similarly to FIG. 1A, in FIG. 2A, processing logic 201 is coupled to drive directional ultrasonic emitter 115 to focus ultrasonic signal 117 to different locations in three-dimensional space, via output X1. Processing logic 201 is also coupled to selectively activate IR illuminator 151 via output X2, in the illustrated embodiment. System 200 may include a plurality of discrete devices that incorporate components of system 200, in some embodiments.

Imaging module 260 includes image pixel array 270 and filter(s) 273. In FIG. 2A, imaging system 200 also includes a directional ultrasonic emitter 115 coupled to be driven by processing logic 201. SLM 210 includes an infrared emitter 205, an infrared light director 206 (illustrated in FIG. 2C), and a display pixel array 213. Display pixel array 213 is a transmissive pixel array, in FIG. 2A.

Processing logic 201 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 201 to store instructions to execute operations and/or store data. A "memory" or "memories" described in this disclosure may include volatile or non-volatile memory architectures.

With ultrasonic signal 117 focused on voxel 133 in diffuse medium 130, IR illuminator 151 is selectively activated to emit general illumination emission 152 and a portion of emission 152 encounters voxel 133.

In FIG. 2B, the wavelength-shifted portion of the general illumination emission 152 is illustrated as shifted infrared imaging signal 243. Being influenced by ultrasonic signal 117, shifted infrared imaging signal 243 has a different wavelength (lambda-two) than general illumination emission 152 (lambda-one).

System 200 receives (at least a portion of) shifted signal 243. An input optic 247 may optionally be included in system 200. Input optic 247 may receive shifted signal 243 and focus the shifted signal 243 to be incident on image pixel array 270. In one embodiment, input optic 247 is configured to filter out an angled portion of the shifted signal 243, as described with regard to an embodiment of input optic 147.

Still referring to FIG. 2B, reference emitter 255 is configured to selectively emit an infrared reference light having the lambda-two wavelength so that infrared reference wavefront 257 interferes with the incoming shifted signal 243. Reference emitter 255 may include one or more laser diodes and reference director optic 256 in optical structure 280 may direct the lambda-two infrared reference light to image pixel array 270 as a substantially uniform infrared reference wavefront 257. Processing logic 201 is coupled to selectively activate reference emitter 255 via output X3, in the illustrated embodiment.

A linear polarizer may be included in system 200 to polarize shifted signal 243 to have the same polarization orientation as infrared reference wavefront 257. Reference emitter 255 may generate linear polarized light which imparts a polarization orientation to infrared reference wavefront 257. The linear polarizer may be included in optic 247, filter 273, or optical structure 280.

Shifted signal 243 may encounter input optic 247, display pixel array 213, and optical structure 280 prior to becoming incident upon image pixel array 270. The shifted signal 243 interferes with infrared reference wavefront 257 and image pixel array 270 captures an infrared image of the interference between shifted signal 243 and infrared reference wavefront 257. To allow shifted signal 243 to pass through display pixel array 213, each of the display pixels of the display pixel array 213 may be driven to a transmissive state while IR illuminator 151 and reference emitter 255 are activated.

In one embodiment, reference director optic 256 is configured to deliver the infrared reference wavefront 257 to the image pixel array 270 at an angle to a pixel plane of the image pixel array 270. Processing logic 201 is coupled to initiate the image capture by image pixel array 270 via output X5, in the illustrated embodiment.

In the illustrated embodiment, an infrared filter 273 is disposed between optical structure 280 and image pixel array 270. Infrared filter 273 may include the same configuration as infrared filter 173. Image pixel array 270 may include the same configuration as image pixel array 170. Image pixel array 270 is communicatively coupled to optical transform logic 250 to send the captured infrared image(s) to optical transform logic 250 for further processing. Optical transform logic 250 is coupled to image pixel array 270 via communication channel X7, in the illustrated embodiment. Optical transform logic 250 is coupled to receive the captured infrared image from the image pixel array 270 and provide a holographic pattern to be driven onto the display pixel array 213. The optical transform logic 250 is configured to extract phase data of the interference captured by the infrared image and the holographic pattern is generated from the phase data.

Referring now to FIG. 2C, display pixel array 213 is configured to generate an infrared holographic imaging signal 244 according to a holographic pattern driven onto the array 213. Optical transform logic 250 is coupled to provide the array 213 the holographic pattern to array 213 via communication channel X8.

In FIG. 2C, display pixel array 213 is illustrated as a transmissive LCD that is illuminated by infrared wavefront 207. In the illustrated embodiment, infrared emitter 205 is coupled to be driven by output X4 of processing logic 201. When processing logic 201 turns on (activates) IR emitter 205, infrared light propagates into IR light director 206. IR light director 206 redirects the infrared light toward display pixel array 213. IR emitter 205 is an infrared laser diode that emits monochromatic infrared light, in one embodiment. In embodiments of the disclosure, reference emitter 255 and IR emitter 205 may output laser light received from a same narrow band laser and optical fibers may provide the laser light to emitters 255 and 205 from the laser.

In the illustrated embodiment, processing logic 201 selectively activates infrared emitter 205 and infrared light director 206 directs the infrared light to illuminate display pixel array 213 as infrared wavefront 207 while the holographic pattern is driven onto array 213. Infrared wavefront 207 is the same wavelength as infrared reference wavefront 257. Processing logic 201 may deactivate reference emitter 255 while display pixel array 213 is being illuminated by infrared wavefront 207. Processing logic 201 may be configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

Display pixel array 213 generates an infrared holographic imaging signal 244 when the holographic pattern is illuminated by infrared wavefront 207 and the infrared holographic imaging signal 244 exits system 200 as a reconstruction (in reverse) of the shifted signal 243 that entered system 200. Reconstructed signal 244 follows (in reverse) whatever scattered path that shifted signal 243 took from voxel 133 to the display pixel array 213 so reconstructed signal 244 is essentially "focused" back onto voxel 133.

Voxel 133 may absorb or scatter reconstructed signal 244 according to biological characteristics of voxel 133 and sensors may measure an exit signal 245 of the reconstructed signal 244 that encounters voxel 133. System 200 may optionally include a sensor 190 coupled to processing logic 201 via an input/output X9 to initiate light measurement of exit signal 245 and pass the light measurement to processing logic 201. Although exit signal 245 is illustrated as being directed to sensor 190, the illustrated exit signal 245 is only a portion of the exit signal 245 that will be generated from signal 244 encountering voxel 133 and exit signal 245 will have many exit points from diffuse medium in addition to the illustrated portion of exit signal 245. The sensors that measure this exit signal may simply measure the amplitude of the exit signal. In one embodiment, the image pixel array 270 is used to measure the amplitude and/or phase of exit signal 245. The amplitude and/or phase of the exit signal 245 may be used to generate an image of diffuse medium 130. A reconstructed signal 244 may be directed to voxel 133 multiple times (with multiple corresponding measurements of exit signal 245) so that biological changes in voxel 133 may be recorded over a time range.

System 200 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array 213 gives display pixel array 213 the ability to generate steerable holographic infrared beams that can focus the reconstructed signal (e.g. 244) to different voxels in three-dimensional space to facilitate the raster scanning of diffuse medium 130.

In one embodiment, processing logic 201 is configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

In system 200, image pixel array 270 is disposed in a parallel plane to display pixel array 213. However, in some embodiments, image pixel array 270 may be angled to increase the signal of interference between the infrared reference wavefront 257 and shifted signal 243. In system 100, image pixel array 170 is illustrated as being in a plane that is orthogonal to display pixel array 113. However, in some embodiment, image pixel array 170 may be angled to increase the signal of interference between the infrared reference wavefront 157 and shifted signal 143.

Although not specifically illustrated in FIGS. 1A-2C, infrared illuminator 151, reference wavefront generator 155 and infrared emitter 105 may be fiber optic outputs that are provided light via fiber optic from a single laser source. Similarly, infrared illuminator 151, reference emitter 255, and infrared emitter 205 may be provided light via fiber optic from a single laser source. The light from the single laser source may be modulated (e.g. by an acoustic optical modulator) to direct the laser light to the proper fiber optic for illumination. A micro-electro-mechanical system (MEMS) mirror, a digital micromirror device (DMD), or a mirror galvanometer may be used to selectively couple light from a single source into different fiber optic paths, in different embodiments. The light from the single laser source may also be selectively wavelength-shifted (e.g. by an acoustic optical modulator) to provide IR illuminator 151 with lambda-one wavelength light and to provide reference elements 105, 205, 155, and 255 with lambda-two wavelength light.

Figure 3:
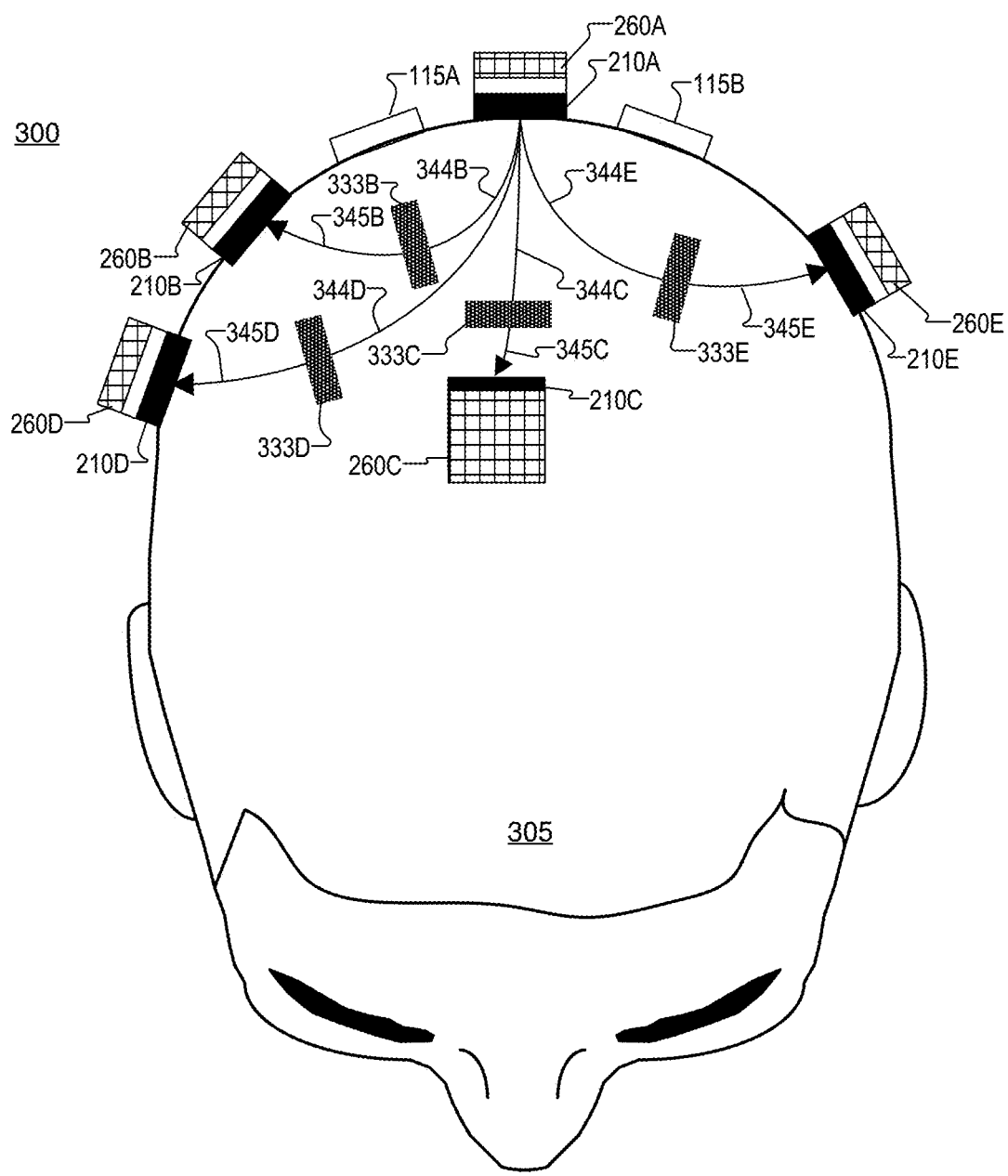
FIG. 3 illustrates an example placement of components of an imaging system in relationship to a human head, in accordance with an embodiment of the disclosure.

FIG. 3 illustrates an example placement of components of an imaging system 300 in relationship to a human head, in accordance with an embodiment of the disclosure. FIG. 3 is a top-down view of a human head 305. Imaging system 300 includes SLMs 210A-210E and imaging modules 260A-260E arranged as in system 200, and directional ultrasonic emitters 115A and 115B. Of course, SLMs 110 and imaging modules 160 may also be used instead of SLMs 210 and imaging modules 260 in imaging system 300. FIG. 3 shows that SLM 210A may generate multiple reconstructed infrared signals 344 that are directed to image different voxels 333 of the brain while the exit signals 345 are imaged by different imaging modules 260. The other SLMs 210B-210E may also generate reconstructed infrared signals 344 (not illustrated) directed to voxels where the exit signals are imaged by each of imaging modules 260A-E. Scientific literature suggests that the penetration depth of infrared light into tissue is around 10 cm so multiple SLMs 210 and imaging modules 160 may be needed to image the entire brain or other tissue. Although not illustrated, sensors 190 may also be placed around a diffuse medium such as human head 305 to measure the exit signals 345. A wearable hat may include system 300 so that system 300 can be worn as a wearable, in some embodiments. Other wearables may also include all or part of system 300.

Figure 4A:
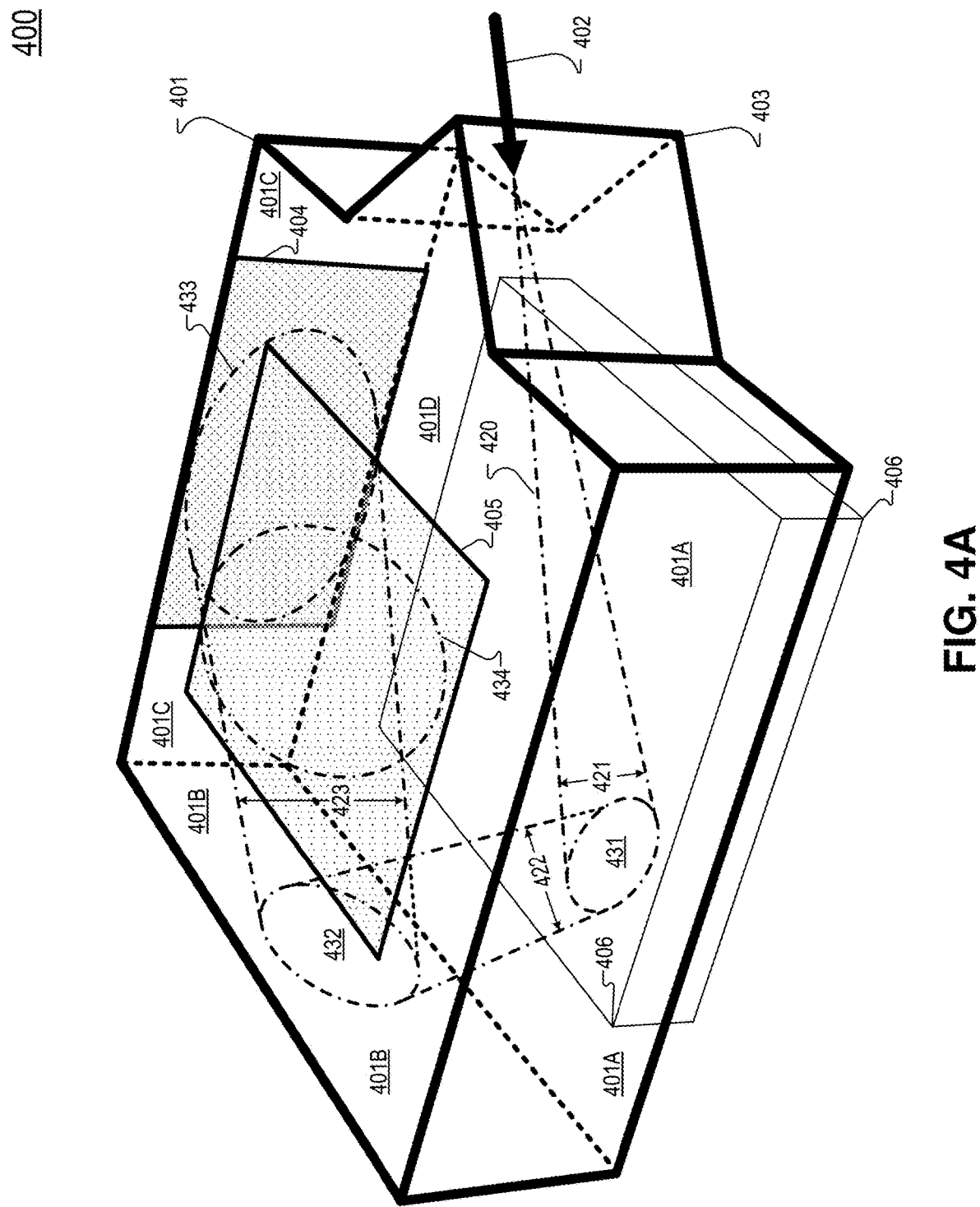
FIGS. 4A-4D illustrate an example refractive component having two reflection surfaces and two diffractive optical elements, in accordance with aspects of the disclosure.

FIG. 4A illustrates an optical element 400 including a refractive component 401 that is made of a refractive material such as glass or acrylic. The refractive material may be a high-index material having a refractive index of 1.4 or greater. In an embodiment, the refractive material has a refractive index of 1.5 or greater. In an embodiment, the refractive material has a refractive index of 1.52. The shape of the example optical element 400 illustrated in FIG. 4A is an extruded rectangle coupled with an extruded triangle prism feature 403. The extruded rectangle and extruded prism feature 403 may be fabricated from a contiguous refractive material. Refractive component 401 includes a fiber entry surface configured to receive a reference beam from an optical fiber 402 into the refractive component. Refractive component 401 also includes a first reflection surface 401A and a second reflection surface 401B. First reflection surface 401A may be offset approximately 90 degrees from the plane of second reflection surface 401B. First reflection surface 401A and/or second reflection surface 401B may be polished surfaces to facilitate total internal reflection (TIR) for an in incident light beam. In an embodiment, a reflection layer (e.g. silver) is formed on all or a portion of first reflection surface 401A and/or second reflection surface 401B to assist in the reflection of an incident light beam. The portions of first reflection surface 401A and/or second reflection surface 401B that do not receive the light beam may be coated with an absorbing black coating to keep stray light out of refractive component 401.

FIG. 4A shows that first diffractive optical element (DOE) 404 is optically coupled with surface 401C of refractive component 401 and second DOE 405 is optically coupled with surface 401D of refractive component 401. FIG. 4A also includes an image sensor 406.

Figure 4B:
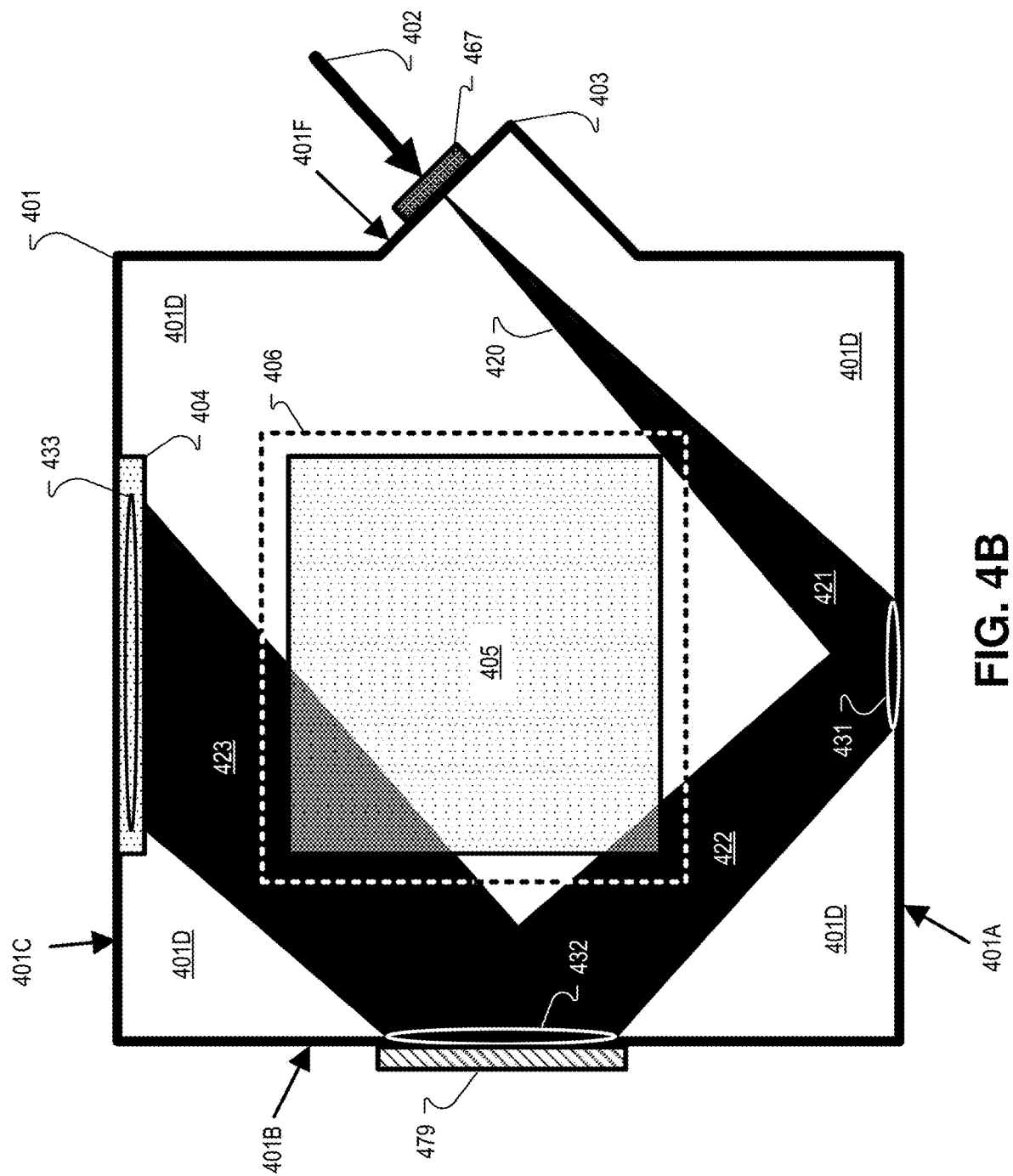

FIG. 4B illustrates a top view of refractive component 401 through surface 401D. FIG. 4B illustrates that an antireflection (AR) layer 467 may be disposed on a fiber entry surface 401F that receives the infrared reference beam from optical fiber 402. Fiber entry surface 401F and the first reflection surface 401A are offset by approximately 45 degrees, in some embodiments. Fiber entry surface 401F is orthogonal to the reference beam 420 as the reference beam 420 exits the optical fiber 402, in some embodiments. Surface 401A and surface 401C may be coplanar. Surface 401A and surface 401B are orthogonal, in some embodiments. The dimensions of a pixel plane having image pixels of image sensor 406 may be smaller than the illustrated dimensions in FIG. 4B.

Figure 4C:
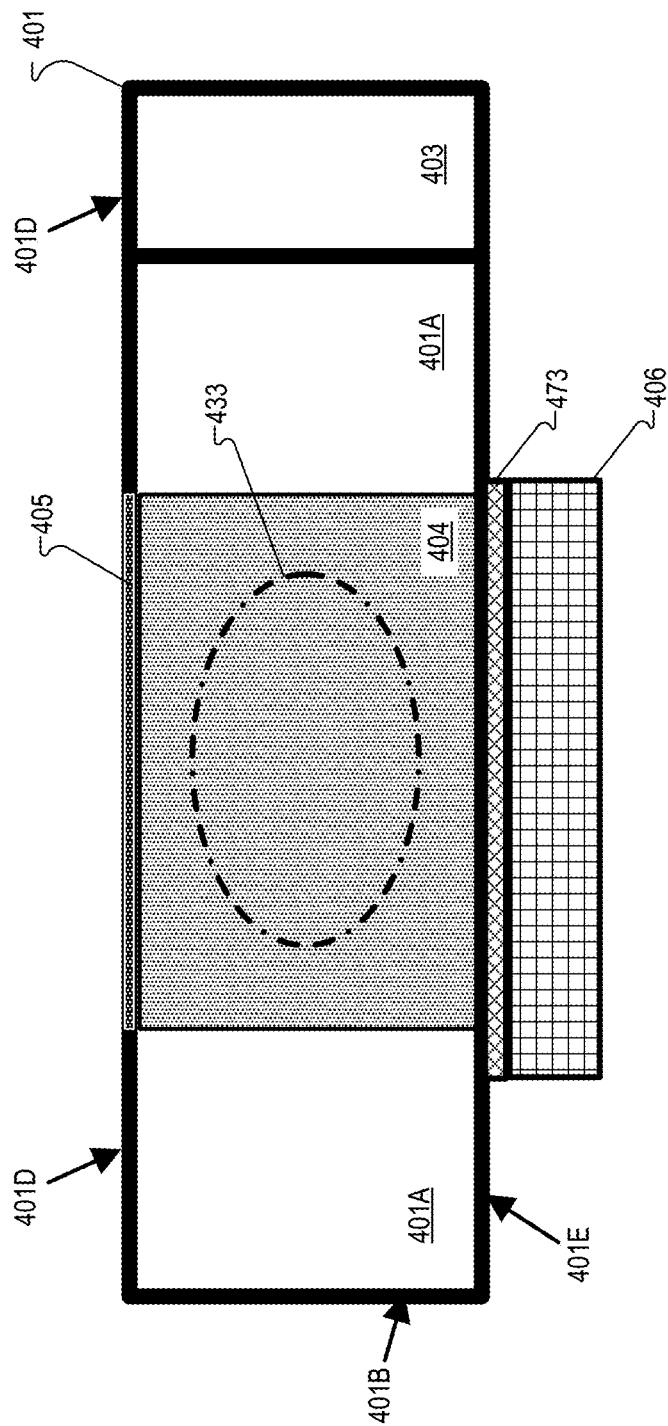

FIG. 4C illustrates a side view of refractive component 401 and shows that a bandpass filter 473 may be disposed over image sensor 406 to filter out light that is not of the wavelength of a reference wavefront and/or an object beam. Bandpass filter 473 may block all visible light. Bandpass filter 473 may be disposed in alternative positions between second DOE 405 and image sensor 406. Surface 401E and surface 401D of refractive component 401 may be coplanar. Surface 401E may include a AR coating to avoid unwanted reflections.

Figure 4D:
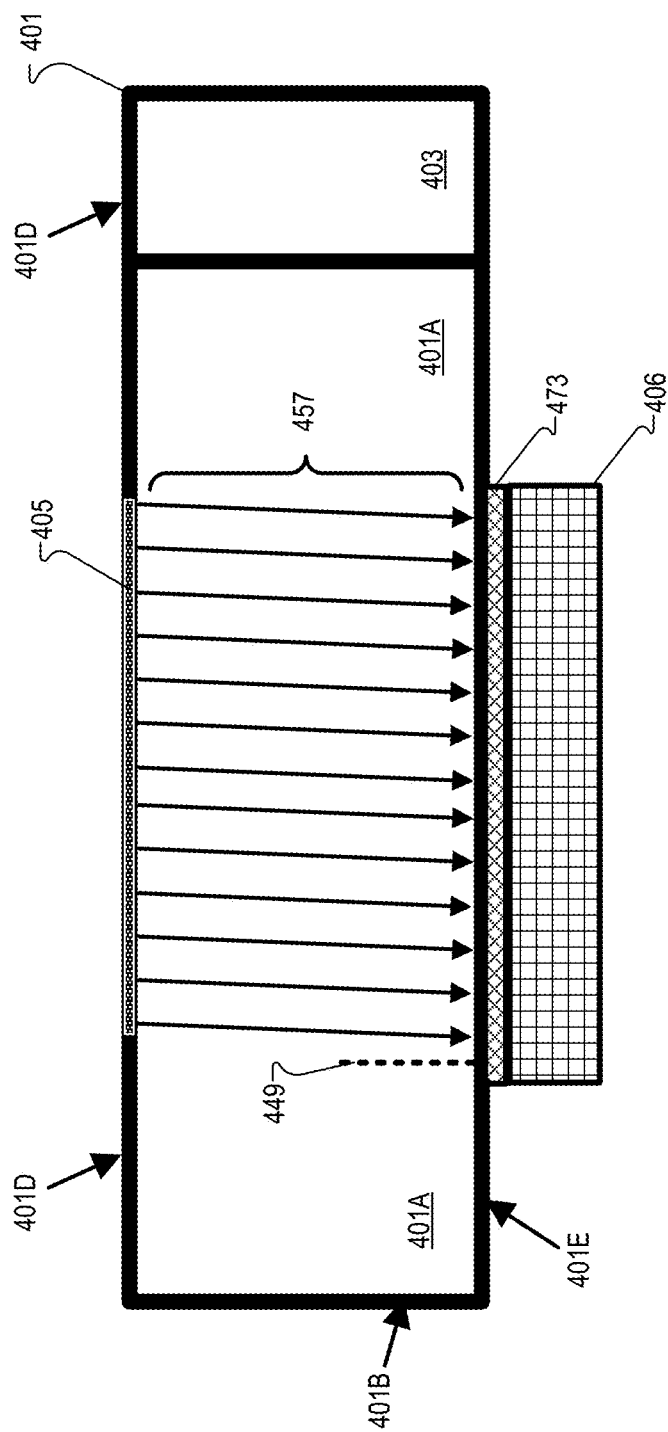

FIG. 4D illustrates a reference wavefront 457 directed to the image sensor 406 by second diffractive optical element 405 at an angle offset with respect to a vector that is orthogonal to a pixel plan of image sensor 406. The reference beam 420 may propagate in a refractive material of the refractive component 401 from when the reference beam 420 encounters the fiber entry surface 401F until when the reference beam 420 exits the refractive component 401 subsequent to encountering the second DOE 405.

Referring again to FIG. 4A, in operation, optical fiber 402 provides a reference beam 420 that is received into refractive component 401. The reference beam 420 may be an infrared reference beam. Reference beam 420 may be a coherent infrared beam generated by a laser. The diameter of the reference beam 420 may be approximately 6 microns as it exits optical fiber 402, for example. Optical fiber 402 may be a single mode fiber. However, a reference wavefront that illuminates an image sensor would be much wider (e.g. 4 mm×4 mm or larger).

To generate a wider reference wavefront, refractive component 401 may utilize a higher index refractive material to expand the reference beam 420 by effectively lengthening the optical path of reference beam 420 with smaller physical dimensions. FIG. 4A shows that the reference beam 420 expands as reference beam portion 421 inside the refractive component 401 and encounters surface 401A as beam spot 431. The reference beam 420 reflects off of first reflecton surface 401A and continues to widen as reference beam portion 422. The reflection of reference beam 420 off of surface 401A may be due to TIR or from reflecting off a mirrored surface disposed on surface 401A.

Reference beam portion 422 encounters surface 401B as beam spot 432 and reflects off of surface 401B and continues to widen as reference beam portion 423. The reflection of reference beam 420 off of surface 401B may be due to TIR or from reflecting off a mirrored surface disposed on surface 401B. FIG. 4B illustrates a reflective layer 479 (e.g. mirrored silver deposition layer) coupled with surface 401B to facilitae reflection of reference beam 420. The dimensions of reflective layer 479 is exaggerated for illustration purposes although the depth of an actual reflection layer may be less than 1 micron thick in some contexts.

Reference beam portion 423 continues to expand until encountering first DOE 404 disposed along surface 401C of refractive component 401. In some embodiments, a microlouver film layer may be disposed behind DOE 404 to absorb light (if any) that passes through DOE 404. First DOE 404 is configured to receive the reference beam from the second reflection surface 401B and configured to collimate and redirect reference beam portion 423 to second DOE 405. FIG. 4 illustrates that reference beam 420 has expanded to the size of beam spot 433 which is wider than beam spot 432, which is wider than beam spot 431. Since first DOE 404 collimates reference beam 420, beam spot 434 on second DOE 405 may be the same or similar size to beam spot 433. In the illustrated embodiment, reference beam 420 expands as it propagates along an optical path from the fiber entry surface 401F to the first reflection surface 401A to the second reflection surface 401B and to the first DOE 404, in that order.

First DOE 404 may be a replicated surface relief hologram that replicatively directly in the refractive material of refractive component 401. The surface relief hologram may be fabricated in a subtractive process that selectively removes the refractive material from refractive component 401. In an embodiment, the surface relief hologram may be molded into refractive component 401. The surface relief hologram may be metalized with a metallic layer deposition. In one embodiment, first DOE 404 includes a volume phase holograme created in a photopolymer it dichromated gelatin that is optically coupled to surface 401C to receive reference beam portion 423. This can either be formed interferometrically or by computer generation and E-beam (or other means) formed then replicated to the surface of the glass (ion etching is a possibility).

Second DOE 405 may be a linear grating or a volume hologram. Second DOE 405 partially transmissive and partially reflective. If a surface relief grating is utilized for DOE 405, the surface structure can be coated with a high-index material such as Zinc Selenide (n–~2.5) then laminated with glass using a suitable cement such as epoxy or UV cured polymer. If a phase grating method is selected for DOE 405, then Dichromated Gelatin or Photopolymer mediums can be used to form an appropriately thick coating. These materials can then be over-laminated. Second DOE 405 is configured to receive the collimated reference beam from first DOE 404 and further configured to redirect the collimated reference beam through refractive component 401, out surface 401E, to be incident on image sensor 406 as reference wavefront 457, as illustrated in FIG. 4D. FIG. 4D illustrates that second DOE 405 is configured to direct the reference beam to the image sensor 406 at an offset angle from a vector 449 normal to a pixel plane of the image sensor. The offset angle may be between 5 and 10 degrees. In an embodiment, the offset angle is approximately 7 degrees. Second DOE 405 may be approximately coplanar with a pixel plane of image sensor 406. First DOE 404 and/or second DOE 405 may be index matched to the refractive material of refractive component 401.

Figure 5:
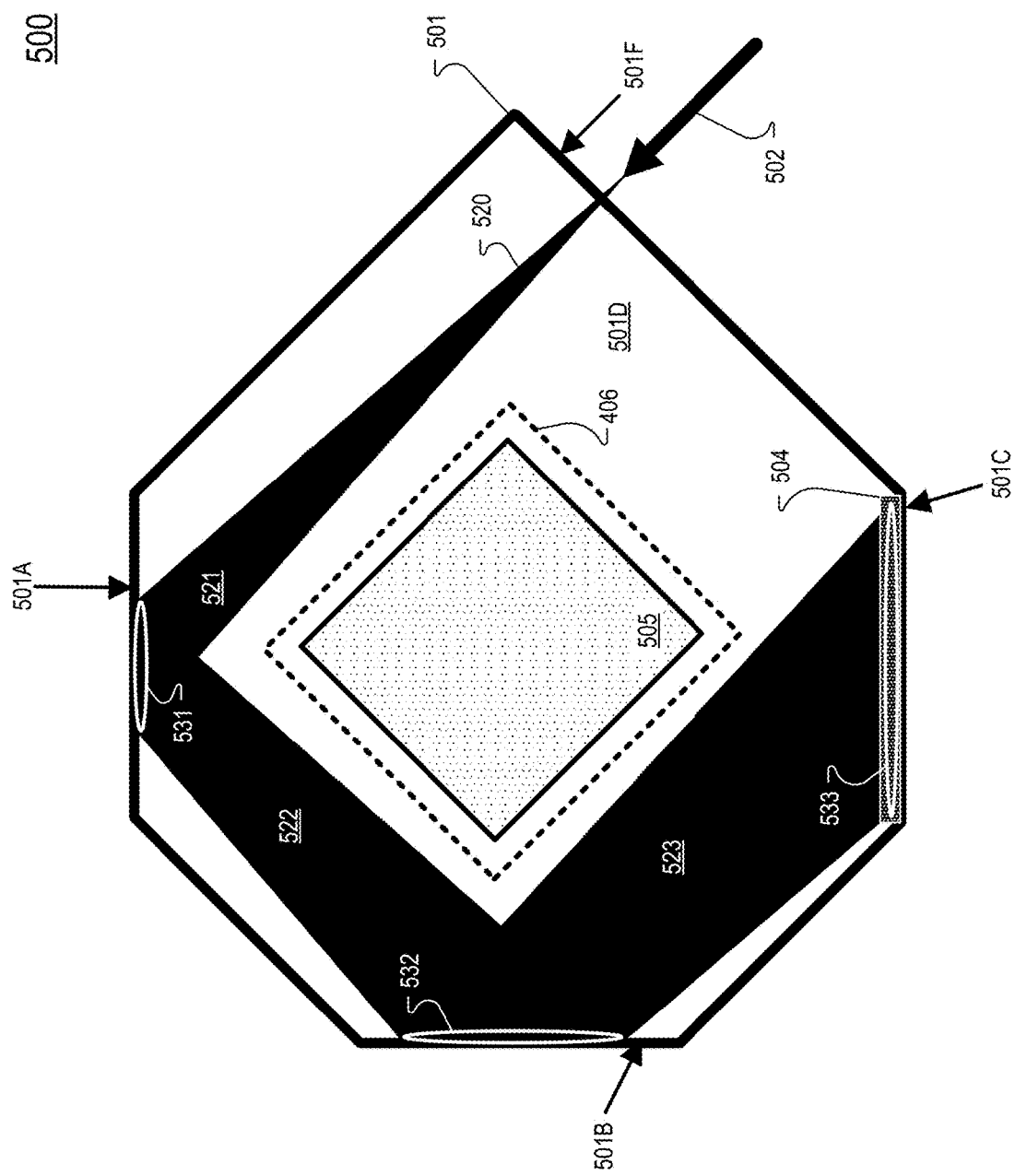
FIG. 5 illustrates an example refractive component, in accordance with aspects of the disclosure.

FIG. 5 shows a top view of an optical element 500 including refractive component 501 that has an alternative shape to refractive component 401, in accordance with aspects of the disclosure. The view of FIG. 5 is looking through surface 501D of refractive component 501. Refractive component 501 includes a fiber entry surface 501F to receive reference beam 520 from optical fiber 502. FIG. 5 illustrates that in some embodiments, an air gap exists between the optical fiber and the fiber entry surface or the refractive component. In FIG. 5, surface 501A may be offset approximately 90 degrees from surface 501B. Surface 501A and 501C may be coplanar. Surfaces 501A may be offset 45 degrees from surface 501F.

Reference beam 520 expands as reference beam portion 521, reflects off of reflection surface 501A, continues to expand as reference beam portion 522, reflects off of reflection surface 501B, and continues to expand as reference beam portion 523 until encountering DOE 504 along surface 501C. Beam spots 531 increases in size to beam spot 532 that increases in size to beam spot 533 as reference beam 520 expands. DOE 504 is configured similarly to DOE 404 and is configured to collimate reference beam 520 and direct the reference beam to DOE 505. DOE 505 is configured similarly to DOE 405 and directs reference beam 520 out of refractive component 501 as a reference wavefront incident on image sensor 406.

Figure 6:
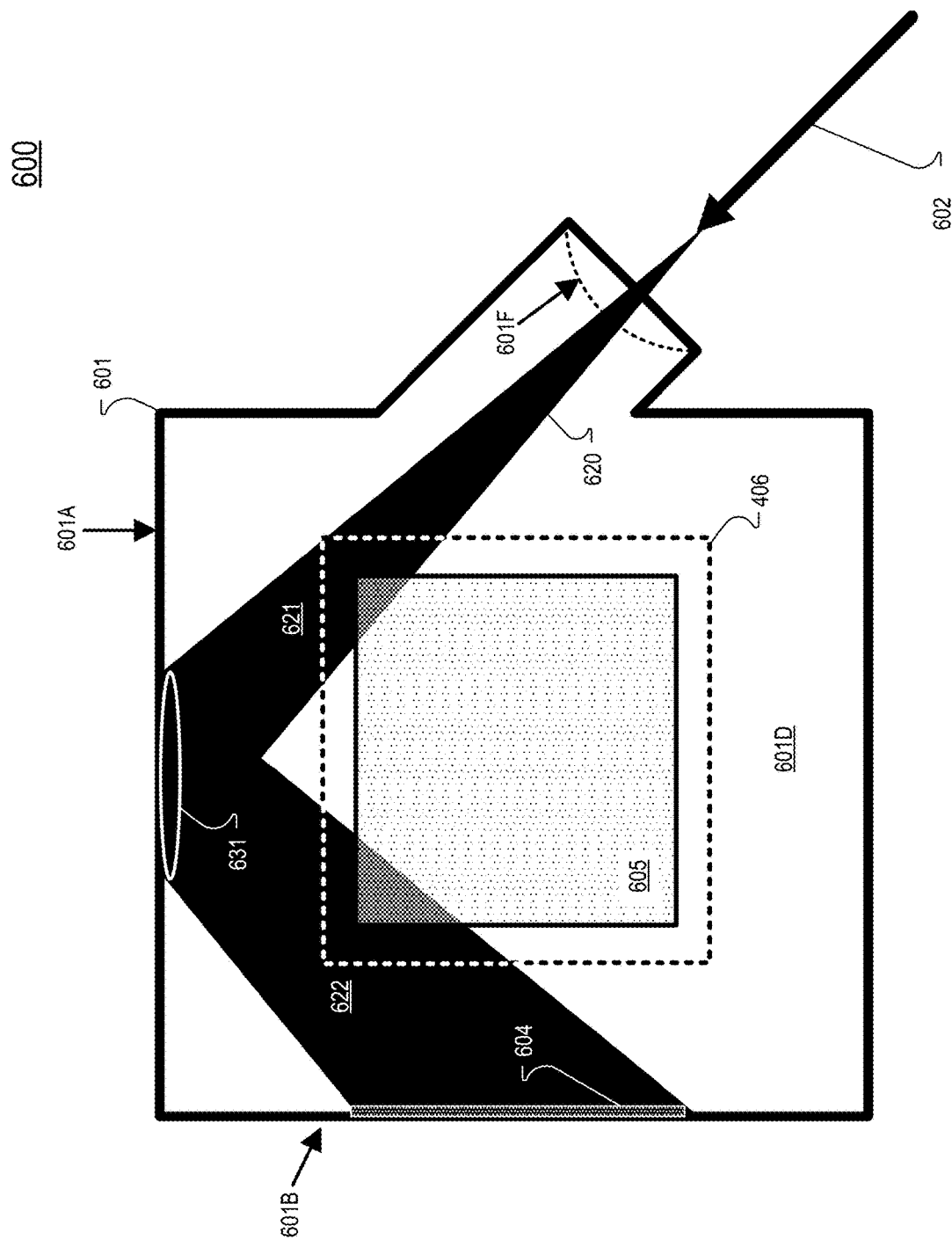
FIG. 6 illustrates an example refractive component including an integrated divergent lens, in accordance with aspects of the disclosure

FIG. 6 shows a top view of an optical element 600 including refractive component 601 that has an alternative shape to refractive components 401 and 501, in accordance with aspects of the disclosure. The view of FIG. 6 is looking through surface 601D of refractive component 601. Refractive component 601 includes a fiber entry surface 601F to receive reference beam 620 from optical fiber 602. FIG. 6 illustrates that in some embodiments, the fiber entry surface may include a concave curvature to increase a divergence of reference beam 620 within refractive component 601. In FIG. 6, surface 601A may be offset approximately 90 degrees from surface 601B. The concave curvature of refractive component 601 may be included in a contiguous refractive material of refractive component 601.

Reference beam 620 expands as reference beam portion 621, reflects off of reflection surface 601A and continues to expand as reference beam portion 622 until encountering DOE 604 along surface 601B. Hence, in FIG. 6, only one reflection surface 601A is utilized. Including a divergent lensing function on the fiber entry surface 601F may allow for fewer reflection surfaces and/or a more compact refractive component 601. DOE 604 is configured similarly to DOE 404 and is configured to collimate reference beam 620 and direct the reference beam to DOE 605. DOE 605 is configured similarly to DOE 405 and directs reference beam 620 out of refractive component 601 as a reference wavefront incident on image sensor 406.

Figure 7:
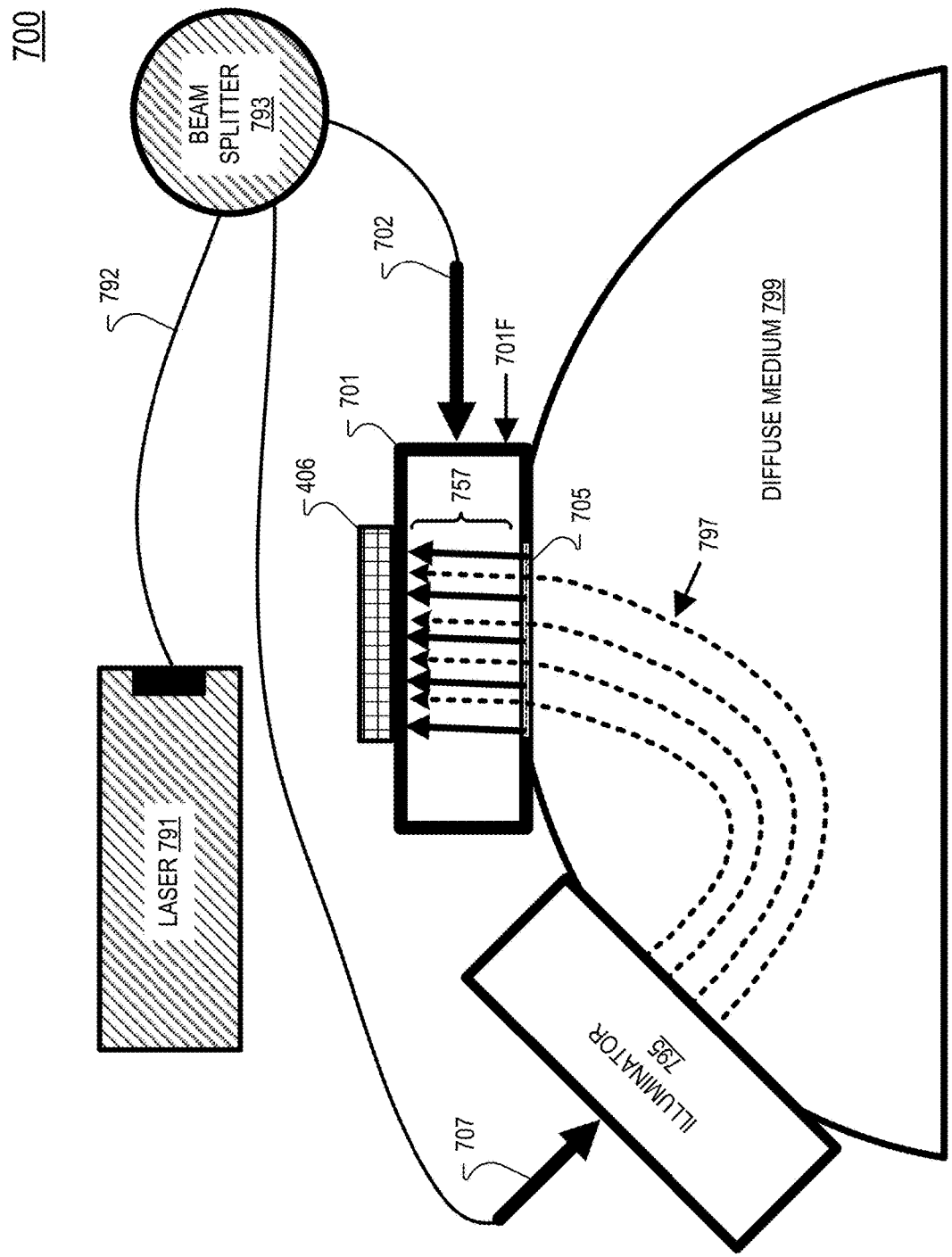
FIG. 7 illustrates and example optical system or device includes a laser, a beam splitter, and a refractive component, in accordance with aspects of the disclosure.

FIG. 7 illustrates an imaging system or imaging device 700 that includes a laser 791, a beam splitter 793, an illumination aperture 795, and a refractive component 701, in accordance with aspects of the disclosure. Laser 791 is configured to emit infrared laser light having a narrow linewidth into optical fiber 792. Beam splitter 793 received the infrared laser light and directs a portion of the infrared laser light to optical fiber 707 into illuminator aperture 795. The remaining portion of the infrared laser light is directed by beam splitter 793 into optical fiber 702 and into refractive component 701. At least a portion of the infrared illumination light directed into diffuse medium 799 by illuminator aperture 795 is scattered by diffuse medium 799 into refractive component 701 as infrared exit signal 797 (object beam). The embodiments of refractive components 401/501/601 may be used as refractive component 701, for example. At least a portion of the infrared exit signal 797 passes through DOE 705 and interferes with infrared reference wavefront 757 to generate an interference pattern upon the pixels of image sensor 406. The embodiments of second DOEs 405/505/605 may be used as DOE 705, for example. The image sensor 406 captures an infrared image of the interference pattern that may represent an optical imaging measurement of a voxel that received a focused ultrasound signal (not illustrated) from an ultrasonic emitter (e.g. ultrasonic emitter 115).

Embodiments of the disclosure may be less expensive and easier to manufacture than conventional methods. Common lab practice indicates the use of a beam splitting cube or mirror to introduce a reference beam source to a photosensitive device. These lab practices are appropriate and adequate for experimental purposes but not when a practical, lightweight, and/or hand-held device is desirable. A device could be made using an assembly of cemented prisms, glass spacers and a lens, but that requires numerous cemented surfaces and undesirable air gaps. This results in a high cost device due to the fixturing and hand work required to assemble it and it is difficult to achieve arbitrary exit angles from a cube prism. In contrast, embodiments of the disclosure provide flexibility in the output angles due to the use of holographic elements (e.g. DOE 404 and 405).

Fabrication of the disclosed optical elements may include cutting and polishing a glass slab refractive material to precise dimensions using conventional methods. Any of vacuum coatings, absorption coatings, anti-reflection coatings, or high-index coatings may be formed on the appropriate surfaces of the refractive material. Holographic optical elements may be formed on the appropriate surfaces by one of the following methods: (1) surface relief casting using a flexible master and light cured polymers; (2) surface relief casting following by ion etching to transfer the relief pattern to the glass; (3) application of pre-produced photopolymer grating; or (4) application of pre-produced dichromated gelatin holograms on glass substrates using a compatible adhesive such as epoxy or light cured polymer. The refractive component can then be attached to the photosensitive element (e.g. image sensor). Then, the optical fiber can be optically coupled to the fiber entry surface of the refractive component. The angle of the optical fiber may need to be adjusted to attain the proper beam angle and collimation quality.

Communication channels described in this disclosure may include wired or wireless communications utilizing IEEE 802.11 protocols, BlueTooth, SPI (Serial Peripheral Interface), I²C (Inter-Integrated Circuit), USB (Universal Serial Port), CAN (Controller Area Network), cellular data protocols (e.g. 3G, 4G, LTE, 5G), or otherwise.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An imaging device comprising:
an image sensor configured to capture an image of an interference between a reference beam and an object beam; an optical fiber configured to provide a reference beam; a refractive component including: a fiber entry surface configured to receive the reference beam from the optical fiber into the refractive component; a first reflection surface; and a second reflection surface; a first diffractive optical element (DOE) optically coupled with the refractive component, the first DOE configured to receive the reference beam from the second reflection surface; and a second diffractive optical element (DOE) that is partially transmissive, wherein the first DOE is configured to collimate and redirect the reference beam to the second DOE, the second DOE configured to redirect the reference beam to the image sensor, wherein the image sensor receives the object beam through the second DOE.

2. The imaging device of claim 1, wherein the fiber entry surface is orthogonal to the reference beam as the reference beam exits the optical fiber.

3. The imaging device of claim 1, wherein the reference beam is a coherent infrared beam generated by a laser.

4. The imaging device of claim 1, wherein the second DOE is configured to direct the reference beam to the image sensor at an offset angle from a vector normal to a pixel plane of the image sensor, the offset angle being between 5 and 10 degrees.

5. The imaging device of claim 1, wherein the reference beam propagates in a refractive material of the refractive component from when the reference beam encounters the fiber entry surface until when the reference beam exits the refractive component subsequent to encountering the second DOE.

6. The imaging device of claim 1, wherein a refractive material of the refractive component has a refractive index of greater than 1.5.

7. The imaging device of claim 1 further comprising: an anti-reflection coating disposed on the fiber entry surface.

8. The imaging device of claim 1 further comprising: at least one reflective layer coupled with the first reflection surface.

9. The imaging device of claim 1, wherein the reference beam expands as it propagates along an optical path from the fiber entry surface to the first reflection surface to the second reflection surface, and to the first DOE, in that order.

10. The imaging device of claim 1, wherein the second DOE is approximately coplanar with a pixel plane of the image sensor.

11. The imaging device of claim 1, wherein the fiber entry surface is along a concave curvature to increase a divergence of the reference beam.

12. The imaging device of claim 1 further comprising: a bandpass filter configured to pass a wavelength of the reference beam and block visible light, wherein the bandpass filter is disposed between the second DOE and the image sensor.

13. The imaging device of claim 1, wherein the first DOE includes a volume phase hologram written in a photopolymer or dichromated gelatin.

14. The imaging device of claim 1, wherein an air gap exists between the optical fiber and the fiber entry surface.

15. The imaging device of claim 1, wherein the first reflection surface and the second reflection surface rely on total internal reflection of a refractive material of the refractive component to reflect the reference beam.

16. The imaging device of claim 1, wherein the first DOE is index matched to a refractive material of the refractive component.

17. The imaging device of claim 1, wherein the fiber entry surface and the first reflection surface are offset by approximately 45 degrees.

18. The imaging device of claim 1, wherein the first reflection surface and the second reflection surface are offset by approximately 90 degrees.

19. An imaging device comprising: a laser configured to emit infrared laser light; an illumination aperture configured to receive a first portion of the infrared laser light and direct the first portion of the infrared laser light into a diffuse medium as an infrared imaging signal; an image sensor configured to capture an image of an interference between a reference beam and an exit signal of the infrared imaging signal exiting the diffuse medium; an optical fiber configured to provide a reference beam, wherein the reference beam is a second portion of the infrared laser light; a refractive component including: a fiber entry surface configured to receive the reference beam from the optical fiber into the refractive component; a first diffractive optical element (DOE) optically coupled with the refractive component, the first DOE configured to receive the reference beam; and a second diffractive optical element (DOE) that is partially transmissive, wherein the first DOE is configured to collimate and redirect the reference beam to the second DOE, the second DOE configured to redirect the reference beam to the image sensor, wherein the image sensor receives the exit signal through the second DOE.

20. The imaging device of claim 18, wherein the refractive component is fabricated from a contiguous refractive material.

21. An optical component comprising: a contiguous refractive component having a refractive index of 1.4 or greater, wherein the contiguous refractive component includes: a fiber entry surface configured to receive an input light beam from a fiber optic into the refractive component as an internal beam; and a reflection surface; and a first diffractive optical element (DOE) coupled with the refractive component, the first DOE configured to receive the internal beam subsequent to the internal beam reflecting off of the reflection surface; and a second diffractive optical element (DOE), wherein the first DOE is configured to collimate and redirect the internal beam to the second DOE, the second DOE configured to redirect the internal beam out of the contiguous refractive component.

* * * * *